(12) United States Patent
Wardlaw

(10) Patent No.: US 7,731,901 B2
(45) Date of Patent: Jun. 8, 2010

(54) APPARATUS AND METHOD FOR PERFORMING COUNTS WITHIN A BIOLOGIC FLUID SAMPLE

(75) Inventor: Stephen C. Wardlaw, Lyme, CT (US)

(73) Assignee: Abbott Laboratories, Abbott Park, IL (US)

( * ) Notice: Subject to any disclaimer, the term of this patent is extended or adjusted under 35 U.S.C. 154(b) by 1200 days.

(21) Appl. No.: 11/257,757

(22) Filed: Oct. 25, 2005

(65) Prior Publication Data

US 2007/0087442 A1    Apr. 19, 2007

Related U.S. Application Data

(60) Provisional application No. 60/728,058, filed on Oct. 19, 2005.

(51) Int. Cl.
*G01N 33/00* (2006.01)
*G01N 31/00* (2006.01)
*G01N 15/06* (2006.01)
*G01N 33/48* (2006.01)

(52) U.S. Cl. .............................. 422/73; 422/64; 422/65; 422/66; 422/66.1; 422/72; 436/10; 436/63; 436/165; 436/527

(58) Field of Classification Search .................. None
See application file for complete search history.

(56) References Cited

U.S. PATENT DOCUMENTS

| | | | |
|---|---|---|---|
| 3,447,863 A | 6/1969 | Patterson | |
| 3,879,106 A | 4/1975 | McCormick | |
| 4,022,521 A | 5/1977 | Hall et al. | |
| 4,171,866 A | 10/1979 | Tolles | |
| 4,218,421 A | 8/1980 | Mack, Jr. | |
| 4,338,024 A * | 7/1982 | Bolz et al. | ................... 356/23 |
| 4,447,140 A | 5/1984 | Campbell et al. | |
| 4,883,642 A | 11/1989 | Bisconte | |
| 4,950,455 A | 8/1990 | Smith | ........................ 422/56 |
| 5,039,487 A | 8/1991 | Smith | |
| 5,321,975 A | 6/1994 | Levine et al. | .............. 73/61.71 |
| 5,726,751 A | 3/1998 | Altendorf | |
| 5,812,312 A | 9/1998 | Lorincz | |
| 5,837,547 A | 11/1998 | Schwartz | |

(Continued)

OTHER PUBLICATIONS

Canadian Office Action dated May 12, 2009.

*Primary Examiner*—Jill Warden
*Assistant Examiner*—Neil Turk
(74) *Attorney, Agent, or Firm*—O'Shea Getz P.C.

(57) ABSTRACT

A method and an apparatus for enumerating one or more specific elements within a biologic fluid sample are provided. An embodiment of the method includes the steps of: a) providing a chamber formed between a first planar member that is transparent and a second planar member, which members are separated from one another by a substantially uniform height; b) introducing the biologic fluid sample into the chamber, wherein the chamber height is sized such that the sample extends between the first and second members, and sized relative to the specific elements within the sample such that the specific elements non-uniformly distribute within the sample upon introduction into the chamber; c) examining substantially all of the sample within the chamber and enumerating all of at least one of the specific elements; d) determining the volume of sample contained within the chamber; and e) determining the number of the at least one of the specific elements per unit volume.

17 Claims, 2 Drawing Sheets

U.S. PATENT DOCUMENTS

| | | | |
|---|---|---|---|
| 6,197,593 B1 * | 3/2001 | Deka et al. ................... 436/63 |
| 6,235,536 B1 | 5/2001 | Wardlaw ................... 436/172 |
| 6,252,660 B1 | 6/2001 | Frisch |
| 6,350,613 B1 | 2/2002 | Wardlaw et al. .............. 436/10 |
| 6,551,554 B1 | 4/2003 | Vermeiden et al. |
| 6,632,652 B1 | 10/2003 | Austin et al. |
| 6,667,177 B1 | 12/2003 | Yabusaki ................... 436/10 |
| 6,723,290 B1 | 4/2004 | Wardlaw ................... 422/102 |
| 6,866,823 B2 | 3/2005 | Wardlaw ................ 422/82.05 |
| 6,869,570 B2 | 3/2005 | Wardlaw ................ 422/82.05 |
| 6,929,953 B1 | 8/2005 | Wardlaw ................... 436/63 |
| 6,988,996 B2 | 1/2006 | Roe et al. |
| 7,179,423 B2 | 2/2007 | Bohm et al. |
| 2002/0135772 A1 | 9/2002 | Bornhop |
| 2009/0081773 A1 | 3/2009 | Kaufman |

* cited by examiner

APPARATUS AND METHOD FOR PERFORMING COUNTS WITHIN A BIOLOGIC FLUID SAMPLE

Applicant hereby claims priority benefits under 35 U.S.C. §119(e) of U.S. Provisional Patent Application entitled APPARATUS AND METHOD FOR PERFORMING BLOOD CELL COUNTS, filed Oct. 19, 2005, Ser. No. 60/728,058, the disclosure of which is herein incorporated by reference.

BACKGROUND OF THE INVENTION

1. Technical Field

The present invention relates to chambers for analyzing biologic fluids in general, and to chambers that permit the enumeration of particulate matter within the biologic fluid in particular.

2. Background Information

The complete blood count (CBC) is the most frequently performed set of tests for whole blood and includes a number of separate analyses such as the white blood count (WBC), the red blood cell count (RBC), and platelet count, among others. The methods used vary in completeness of analyte set, complexity and cost of equipment, and per-test cost. The least complex methods, such as the QBC® method described in U.S. Pat. No. 4,156,570, have the least expensive capital costs and are simple to perform, but typically have higher per-test costs. The QBC® method is most suited for point-of-care situations where operator training is minimal and few tests are performed per day. On the other end of the spectrum, large volume blood analyzers used in hospitals or reference laboratories can have a capital cost twenty times greater but a relatively low per-test cost when used on a large volume basis, which makes them much more cost-effective in those settings.

One of the simplest and oldest methods of counting cells involves the use of a hemocytometer. In a hemocytometer, a precise dilution of the blood is made. An approximate amount of that dilution is subsequently placed into a counting chamber with a height sufficient that the diluted sample, when flowing into the chamber, maintains the same uniformity of cells as is found in the diluted samples. That is, the chamber must not selectively concentrate or dilute any of the cells or other elements because of the sample flowing into and through the chamber. This is because only a representative fraction of the cells in a known area of the chamber is counted. If the distribution of cells was skewed, such a count would therefore incorrectly reflect the count of the entire sample.

Larger modem systems, such as the Abbot Cell-Dyn® or the Bayer Advia® are based upon some variation of a flow-cytometer (FC), where a precise quantity of blood is precisely diluted and mixed with reagents in a number-of steps. Fluidic valves route the diluted sample into multiple test areas. As with the hemocytometer, the distribution of cells within the diluent must remain relatively homogeneous so that a count of a representative portion of the diluted sample can represent the count in the original sample. This approach requires a substantial instrumental complexity to the point where the reliability of these instruments is relatively low. In fact, with these larger systems it is not uncommon for preventative maintenance or repairs to be required on a weekly basis, or more often, which requires the skills of specially trained laboratory technologists or service technicians, all of which substantially add to the cost of operation. Another hidden cost of operation is the washing, cleaning and calibration procedures which are required to make the system perform properly.

In the QBC® system, an approximate quantity of blood is placed in a capillary tube, centrifuged and examined. This method, although not requiring an exact sample, does not produce true cell counts and cannot give accurate estimates of cell numbers when very few cells are present.

An intermediate system has been described in U.S. Pat. Nos. 6,723,290; 6,866,823; 6,869,570; and 6,929,953, wherein blood is placed into a single-use disposable for analysis. These patents describe a reliable, low-cost, and easy-to-use method and instrument that can provide the same breadth of analytic data as the above-described flow-cytometric systems. In this system, an approximate quantity of the undiluted sample is placed in a disposable whose characteristics allow the distribution of cells within the sample to remain substantially uniform. The cells in a given imaged field are counted, the volume of that field is determined, and the cell count per volume is then calculated. In this system, as with that of the hemocytometer, only a portion of the sample added to the chamber needs to be counted because the distribution of cells is substantially uniform. This method, however, requires a single-use disposable, which is advantageous for low-volume testing, but which is not specifically intended for high-volume testing.

It would be advantageous to have a system wherein the elements in an undiluted sample of whole blood could be enumerated in a chamber of sufficient thinness so that cell counts and cell morphology could be obtained from a sample, and one wherein the effects of the non-uniform distribution could be mitigated. Such an analytical system would reduce or eliminate fluid handling and precise measurement or dilution of the sample, resulting in a much simpler and less expensive method for such analyses.

DISCLOSURE OF THE INVENTION

A method and apparatus for counting elements within a fluid medium is provided that is simple, accurate and relatively low cost. The method and apparatus is particularly well suited to performing blood cell counts (i.e., WBCs, RBCs, etc.) within a sample of anticoagulated, unlysed whole blood. In the present method, an approximate quantity of sample is placed into a chamber of very small height, generally less than 20 microns, and for counting blood, preferably about four microns. Upon entry into the chamber, the distribution of certain types of elements within the sample changes markedly. The change in distribution for certain elements within the sample is attributable to the size of the elements within the sample relative to the height of the chamber. If a sample of blood is introduced into the chamber, for example, red blood cells within the sample will concentrate at the periphery of the chamber and white blood cells within the sample will concentrate near the chamber sample inlet. The RBCs typically disperse within the sample a greater distance from the inlet than do the WBCs because RBCs are smaller and typically have highly mobile membranes and can conform to tight spaces, while the WBCs are larger and are relatively rigid compared to the RBCs. Although the relatively thin height of the chamber allows easy visualization of the elements, the distribution of elements within the sample is such that there is typically no partial region of the sample that is representative of the entire sample. Consequently, there is no partial region representative of the entire sample that can be counted to give an accurate count of the entire sample. In the present method, in contrast to all other enumeration methods of which we are aware, the entirety of the sample added to the chamber is examined and all of the non-uniformly distributed cells within the sample of the particular type(s) to be examined are enumerated. Once the total number of the non-uniformly distributed cell type to be examined within the sample is known, the count of the non-uniformly distributed cell of that type per unit volume of sample can be calculated by dividing the number of cells counted by the volume contained within the chamber. The phenomenon of non-uniformity of cell distribution within small chambers has been well-known since the beginning of cell counting and has always been avoided as highly undesirable because of the near-impossibility of manually counting all elements within the chamber in order to get an accurate total count. Additionally, the minute sample size used by such a chamber precluded accurate initial measurement of the quantity of sample or the later calculation of the sample volume of the irregularly spread sample within in such a chamber. However, with the recent advent of accurate and rapid digital imaging systems which allows these counts to be made and the total area of the chambered sample calculated, a thin-film chamber can now be used advantageously as a simple and accurate method for obtaining blood cell or other counts.

In some embodiments, the present method for enumerating one or more specific elements within a biologic fluid sample includes the steps of: a) providing a chamber formed between a first planar member that is transparent and a second planar member, which members are separated from one another by a substantially uniform height; b) introducing the biologic fluid sample into the chamber, wherein the chamber height is sized such that the sample extends between the first and second members for at least a portion of the chamber, and wherein the chamber height is sized relative to the one or more specific elements such that the one or more specific elements non-uniformly distribute within the sample upon introduction into the chamber; c) examining substantially all of the sample within the chamber and enumerating all of at least one of the specific elements; d) determining the volume of sample contained within the chamber; and e) determining the number per unit volume of the at least one specific element.

This invention, in contrast to all prior art of which we are aware, examines the entirety of a biologic fluid sample (e.g., undiluted whole blood) present in a thin film confined in a chamber defined by two relatively planar substrates, where the total volume of the sample added to the chamber can be determined. All of at least one of the specific elements within the sample are enumerated, in contrast to all other methods, where only a portion of the sample is examined. The phrase "all of at least one of the specific elements" is intended to mean all of a particular type of the specific elements. If the one or more specific elements includes elements A, B, and C, for example, and the "at least one of the specific elements" refers to element A, then enumerating "all of at least one of the specific elements", would mean enumerating all of the element A's within the sample.

Any chamber formed with at least one transparent wall may be used. The chamber can be produced by techniques such as micro-machining, etching, substrate deposition. The technique described in co-pending U.S. Patent Publication No. 2001-0033808 and U.S. Pat. No. 6,287,870 which use a layer of separator elements to effect the uniform thickness of the chamber, is an example of an acceptable technique.

The present method requires that the sample volume which is introduced into the chamber be substantially accurately known or determinable. The term "substantially accurately" is defined as a volume accuracy that is adequate for the test at hand. The volume determination of the sample can be performed using a number of different techniques, including but not limited to: 1) calculating the sample volume when first deposited by interferometric imaging using optical techniques available from sources such as the Zygo Corporation, of Middlefield, Conn.; or 2) calculating the sample volume following film formation (the film is formed by the sample spreading out within the chamber) measuring the area of the sample film and multiplying this by the average height of the sample film; or 3) using or fabricating a chamber having a precise known volume (i.e., thickness and extent), where the blood sample added would flow into the chamber until it can contain no more blood (i.e., since the total volume of contained blood is known a priori, the total number of enumerated elements is divided by the known volume of the chamber to give the count/volume).

For the purposes of this invention, a reading, or cell enumerating instrument may be similar in function to that shown in co-pending U.S. Patent Publication No. 2002-0028158 and U.S. Pat. No. 6,869,570.

These and other objects, features and advantages of the present invention will become apparent in light of the detailed description of the invention provided below, and as illustrated in the accompanying drawings.

BRIEF DESCRIPTION OF THE DRAWINGS

The principles of the invention are further clarified by referring to the following figures.

DETAILED DESCRIPTION OF THE INVENTION

Figure 1:
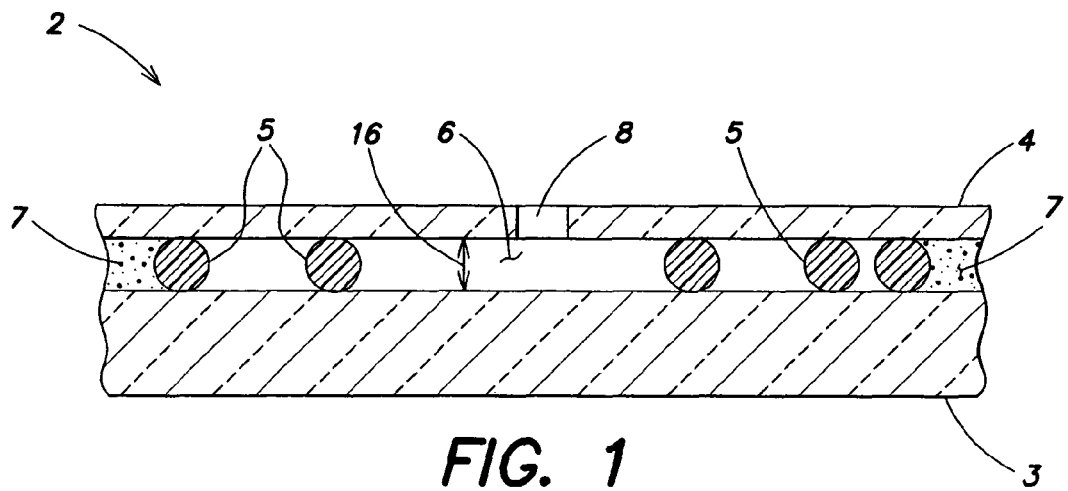
FIG. 1 is a diagram of a chamber according to the teachings of this invention having two transparent surfaces separated by a known and relatively uniform space.

Referring to FIGS. 1-5, the present apparatus for analyzing biologic fluids includes one or more chambers 2 defined by a first planar member and a second planar member, separated from one another by a distance referred to hereinafter as the chamber height 16. At least one of the first planar member and the second planar member is sufficiently transparent so that a biologic fluid sample disposed within a chamber 2 may be imaged. To facilitate the description of the present invention, the planar members are referred to hereinafter as the "top" planar member 4 and the "bottom" planar member 3. The top planar member 4 hereinafter is also described as being transparent. In alternative embodiments, the bottom planar member 3 may be transparent rather than the top planar member 4, or in addition to the top planar member 4.

The planar members 3, 4 can be formed from a variety of materials, having different or identical properties. Patent Cooperation Treaty Patent Publication No. WO/2005/100539 commonly owned with the present application and hereby incorporated by reference in its entirety, discloses examples of acceptable planar members 3, 4. As a further example, the top planar member 4 may be formed from a polyethylene terphthalate (PET) tape having a thickness and width of approximately 25µ and one inch, respectively. The bottom planar member 3 can be similarly formed from PET tape of similar width, having a thickness of approximately 128µ.

Present invention embodiments wherein the planar members 3, 4 are flexible, permit the chambers 2 to be wound on a reel.

Although sidewalls are not required for the practice of this invention, in some embodiments, the chambers 2 are further defined by one or more sidewalls 7. In preferred embodiments, the sidewalls 7 consist of bonding material that extends between the top planar member 4 and the bottom planar member 3. The sidewalls 7 may be positioned to create different chamber configurations. For example, in some embodiments bonding material may be applied so that one or more sidewalls 7 extend substantially across the width of the planar members 3, 4. In other embodiments, the sidewalls 7 may be formed in a shape that substantially or completely encloses the chamber 2. The embodiment shown in FIG. 3, for example, shows an elliptical shaped side wall 7 enclosure formed by bonding material. The sidewalls 7 may be made of material other than bonding material.

For sidewall 7 embodiments that use bonding material, the bonding material may consist of any of a variety of different materials that adhere to the planar members 3, 4, or interact with the planar members 3, 4 sufficiently to create a seal adequate to retain the sample within the chamber 2. In preferred embodiments, the bonding material is a material with adhesive properties that attaches the planar members 3, 4 to one another. Bonding materials that include a light-curing adhesive, of which numerous examples are readily available, are particularly useful.

In some embodiments, the present invention includes one or more separator elements 5 disposed within the chamber. Examples of acceptable separator elements 5 are disclosed in co-pending U.S. patent application Ser. Nos. 09/885,193 and 09/366,881, both of which are hereby incorporated by reference in their entirety, and PCT Patent Application No. PCT/2005/011602. An example of an acceptable separator element 5 is a spherical bead made of polystyrene, of known and precisely controlled diameter. In embodiments wherein the planar members 3, 4 are formed from substantially rigid material, there may be no need for the separator elements 5, depending upon the actual configuration of the chamber. As described in PCT/2005/011602, the separator element 5 height is such that in an analysis of undiluted anticoagulated blood the WBC's within the sample are slightly compressed between the planar members 3,4. As a result, the WBC's within the chamber tend to become entrapped within the chamber and are generally found in highest concentration near the inlet of the chamber; i.e., non-uniformly distributed within the chamber.

In some embodiments, the top planar member 4 includes one or more of an inlet port 8 and a vent aperture 10. The inlet port 8 provides access to the chamber for the biologic sample. The vent aperture 10 provides a passage through which air may escape as the biologic sample is introduced into the chamber 2. In embodiments where at least a portion of the chamber 2 is open (e.g., where the side walls of the chamber 2 do not form a complete enclosure), the inlet port 8 and vent aperture 10 may be omitted To illustrate the utility of the present invention apparatus, the following examples of methods for using the apparatus are provided. The present invention method and apparatus are not, however, limited to these particular examples.

Figure 2:
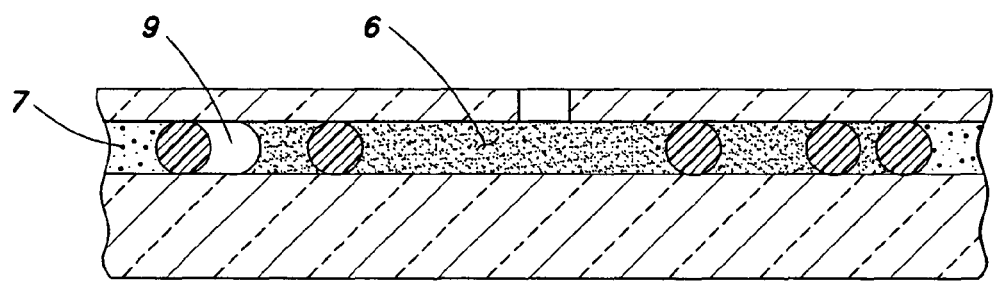
FIG. 2 is a cross section of the chamber diagram of FIG. 1 after a volume of blood has been introduced into the chamber.

Referring to FIG. 2, a chamber 2 is shown after a sample 6 of undiluted anticoagulated, and unlysed whole blood has been added through fill hole 8. In some applications, it is not necessary that the sample 6 fill the entirety of the chamber 2. In those embodiments where one or both of the top planar member 4 and the bottom planar member 3 are relatively flexible, it is preferable that the chamber 2 not be completely filled, leaving small unfilled areas 9. The unfilled areas 9 are advantageous in such chamber 2 embodiments, because the capillary force from the unfilled areas exerts a strong downward force on the planar members 3, 4 of the chamber 2, which force is helpful in keeping the height 16 of the chamber 2 uniform.

Figure 3:
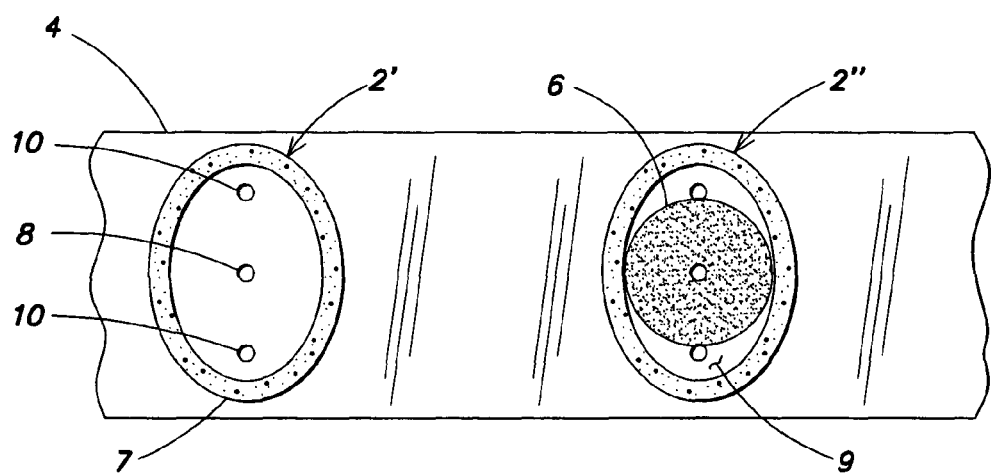
FIG. 3 is a diagrammatic top planar view of a chamber showing a filled and an unfilled chamber.

In a second embodiment, FIG. 3 illustrates a pair of chambers 2', 2" adjacent one another. The chamber 2' disposed on the left shows an unfilled chamber defined in part by a sidewall enclosure 7. The top planar member 4 of the chamber 2' includes an inlet port 8 and a pair of vent apertures 10. A biologic fluid sample 6 (e.g., blood) has been introduced into the chamber 2" disposed on the right through the inlet port 8. The sample 6 has spread from the inlet port 8 to fill the majority of the chamber, leaving small air spaces 9 disposed adjacent the vent apertures 10. Because of the relative magnitudes of the chamber height 16 and the average "thickness" (e.g., diameter) of one or more specific elements (e.g., WBCs, RBCs) present within the sample, the distribution of elements within the sample typically becomes highly non-uniform. A highly non-uniform distribution contrasts strongly with prior art methods that rely upon a uniform distribution of elements to ensure accuracy.

Figure 4:
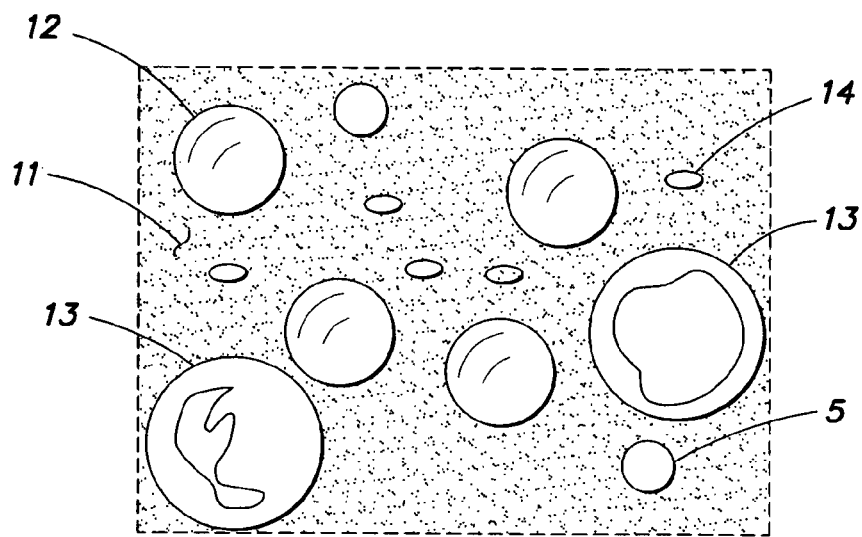
FIG. 4 is an enlarged diagrammatic view of a central region of a chamber.

An example of a non-uniform distribution of elements within a chamber 2 is illustrated in FIG. 4, by showing a diagrammatic representation of a microscopic field near the inlet port. In this representation, the plasma 11 is more prevalent than the RBCs 12. Because of their size, WBCs 13 are also concentrated in this area. Also seen in this figure are the separator particles 5 and platelets 14. In this example, the specific elements to be enumerated, for example, could be one or more of the WBCs 13 or RBCs 12. The elements to be enumerated could also be subsets of the identified elements; e.g., specific types of WBCs, or WBCs having surface epitopes which are selectively stained to be identifiable and separately enumerated, etc.

Figure 5:
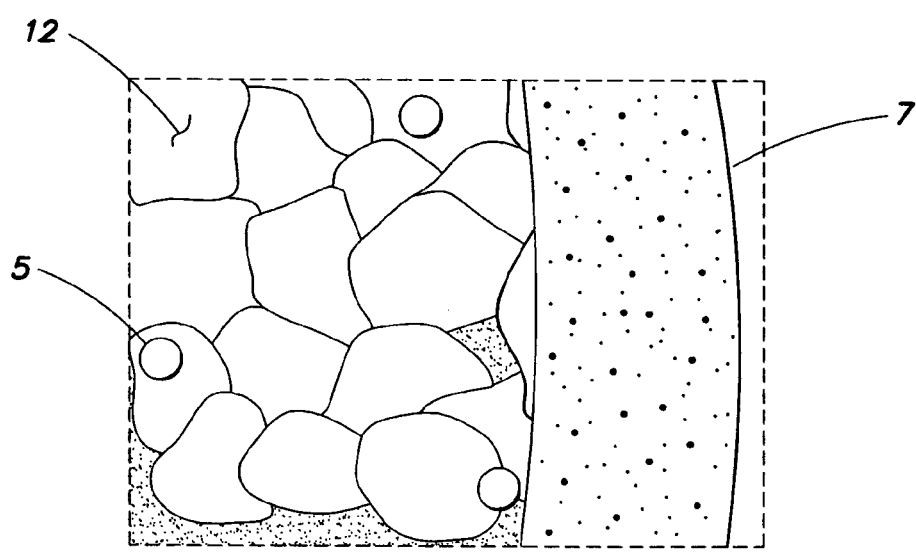
FIG. 5 is an enlarged diagrammatic view of a peripheral region of a chamber.

In contrast, a microscopic field is diagrammatically illustrated in FIG. 5, depicting a portion of the chamber 2 disposed near the chamber sidewall 7. In that field, masses of RBCs 12 are disposed adjacent the side wall 7 and make up the majority of the field.

It is clear from these examples that an accurate enumeration is not practically possible using prior art methods that only consider a fraction of the sample. The present invention method and apparatus, in contrast can provide an accurate enumeration in applications where the elements to be enumerated are not uniformly distributed. At the same time, specific information regarding certain of the specific elements can be obtained (e.g., WBC cell morphology). To obtain an accurate enumeration using the present method, the entirety of the sample is imaged using a digital camera and the image is subject to an analysis which detects and enumerates every one of the specifically targeted non-uniformly dispersed elements disposed within the chamber. Depending upon the area of the sample, this analysis can be performed an image frame at a time as the entire area of the sample is imaged, or a series of images can be 'stitched' together to create a larger image which is analyzed at once. A suitable instrument and software for this are described in U.S. Pat. Nos. 6,866,823; 6,869,570; and 6,929,953. The same image analysis then determines the actual volume of sample within the chamber. Once the count has been completed and the volume determined, the count per unit volume is calculated.

It can be appreciated that this invention can also perform most of the functions of a flow-cytometer by adding fluorescent or other markers to cell-specific ligands and examining the chamber to enumerate which cells have the ligand-marker bound to their surfaces.

Although this invention has been shown and described with respect to the detailed embodiments thereof, it will be understood by those skilled in the art that various changes in form and detail thereof may be made without departing from the spirit and the scope of the invention.

What is claimed is:

1. A method for enumerating cellular elements within a biologic fluid sample, comprising the steps of:
   providing a chamber formed between a first planar member that is transparent and a second planar member, which members are separated from one another by a substantially uniform height;
   introducing an amount of the biologic fluid sample into the chamber sufficient for the sample to extend between the first and second planar members for at least a portion of the chamber, which fluid sample has first cellular elements and second cellular elements;
   sizing the chamber height such that the chamber height relative to a thickness of the first cellular elements within the sample and a thickness of second elements within the sample, causes the cellular elements to non-uniformly distribute within the chamber;
   examining substantially all of the sample within the chamber in an unlysed state and enumerating all of at least one of the first and second elements non-uniformly distributed within the chamber;
   determining the volume of sample contained within the chamber; and
   determining the number of the at least one of the specific elements per unit volume.

2. The method of claim 1, wherein the biologic fluid sample is anticoagulated whole blood.

3. The method of claim 2, wherein the steps of examining, determining the volume, and determining the number utilize digital image analysis.

4. The method of claim 3, wherein the first elements are white blood cells.

5. The method of claim 4, wherein the white blood cells include some white blood cells having surface epitopes which are selectively stained to be identifiable and separately enumerated from other white blood cells.

6. The method of claim 1, wherein the steps of examining, determining the volume, and determining the number utilize digital image analysis.

7. The method of claim 1, wherein all of the first and second elements non-uniformly distributed within the sample are enumerated.

8. The method of claim 1, wherein the thickness of the first elements is greater than the thickness of the second elements.

9. The method of claim 8, wherein the thickness of the second elements relative to the height of the chamber is such that the second elements distribute further distances within the chamber upon introduction of the sample into the chamber than the first elements distribute.

10. The method of claim 9, wherein the chamber is height is equal to or less than twenty microns.

11. The method of claim 10, wherein the first elements are white blood cells and the second elements are red blood cells.

12. The method of claim 1, wherein the height of the chamber relative to the thickness of the first elements is such that the first elements are slightly compressed between the first and second planar members.

13. The method of claim 1, wherein the chamber height is such that the sample is drawn into the chamber by capillary action upon being introduced into the chamber.

14. The method of claim 13, wherein the height of the chamber relative to the thickness of the first elements is such that the first elements tend to become entrapped within the chamber and are concentrated near an inlet of the chamber as the sample is drawn into the chamber.

15. A method for enumerating cellular elements within an anticoagulated whole blood sample, comprising the steps of:
   providing a chamber formed between a first planar member that is transparent and a second planar member, which members are separated from one another by a substantially uniform height;
   introducing an amount of sample into the chamber sufficient for the sample to extend between the first and second members for at least a portion of the chamber, which sample includes cellular elements;
   sizing the chamber height such that the height of the chamber relative to the cellular elements within the sample cause said elements to non-uniformly distribute within the chamber;
   examining substantially all of the sample within the chamber in an unlysed state and enumerating all of at least one of the elements non-uniformly distributed within the chamber;
   determining the volume of sample contained within the chamber; and
   determining the number of at least one of the elements per unit volume of the sample.

16. The method of claim 15, wherein the chamber height is less than twenty microns.

17. A method for enumerating biologic particulates within an anticoagulated whole blood sample, comprising the steps of:
   providing a chamber formed between a first planar member that is transparent and a second planar member, which members are separated from one another by a substantially uniform height;
   introducing an amount of sample into the chamber sufficient for the sample to extend between the first and second members for at least a portion of the chamber, which sample includes biologic particulates;
   sizing the chamber height such that the height of the chamber relative to the biologic particulates within the sample cause the particulates to non-uniformly distribute within the chamber;
   examining substantially all of the sample within the chamber in an unlysed state and enumerating all of at least one of the elements non-uniformly distributed within the chamber;
   determining the volume of sample contained within the chamber; and
   determining the number of at least one of the elements per unit volume of the sample.

* * * * *